US010631800B2

(12) United States Patent
Siewerdsen et al.

(10) Patent No.: US 10,631,800 B2
(45) Date of Patent: Apr. 28, 2020

(54) DUAL-ENERGY CONE-BEAM COMPUTED TOMOGRAPHY WITH A MULTIPLE SOURCE, SINGLE-DETECTOR CONFIGURATION

(71) Applicants: The Johns Hopkins University, Baltimore, MD (US); Carestream Health, Inc., Rochester, NY (US)

(72) Inventors: Jeffrey H. Siewerdsen, Baltimore, MD (US); J. Webster Stayman, Baltimore, MD (US); Wojciech Zbijewski, Baltimore, MD (US); John Yorkston, Rochester, NY (US)

(73) Assignees: The Johns Hopkins University, Baltimore, MD (US); Carestream Health, Inc., Rochester, NY (US)

( * ) Notice: Subject to any disclaimer, the term of this patent is extended or adjusted under 35 U.S.C. 154(b) by 244 days.

(21) Appl. No.: 15/030,818

(22) PCT Filed: Nov. 25, 2014

(86) PCT No.: PCT/US2014/067208
§ 371 (c)(1),
(2) Date: Apr. 20, 2016

(87) PCT Pub. No.: WO2015/081035
PCT Pub. Date: Jun. 4, 2015

(65) Prior Publication Data
US 2016/0262709 A1    Sep. 15, 2016

Related U.S. Application Data

(60) Provisional application No. 61/909,115, filed on Nov. 26, 2013.

(51) Int. Cl.
*A61B 6/00* (2006.01)
*A61B 6/03* (2006.01)

(52) U.S. Cl.
CPC ............ *A61B 6/4007* (2013.01); *A61B 6/032* (2013.01); *A61B 6/4035* (2013.01);
(Continued)

(58) Field of Classification Search
CPC ....... A61B 6/032; A61B 6/4007; A61B 6/482; A61B 6/405; A61B 6/4035
See application file for complete search history.

(56) References Cited

U.S. PATENT DOCUMENTS 5,625,661 A    4/1997  Oikawa
8,102,963 B2 *  1/2012  Shapiro .................. A61B 6/032
                                                                378/8
(Continued)

FOREIGN PATENT DOCUMENTS

DE    102010061889 A1    5/2012
JP       2009125250 A    6/2009
(Continued)

OTHER PUBLICATIONS

International Search Report and Written Opinion of PCT/US2014/067208.

*Primary Examiner* — Dani Fox
(74) *Attorney, Agent, or Firm* — Venable LLP; Henry J. Daley (57) ABSTRACT

The present invention is directed to a system and method for dual-energy (DE) or multiple-energy (spectral) cone-beam computed tomography (CBCT) using a configuration of multiple x-ray sources and a single detector. The x-ray sources are operated to produce x-ray spectra of different energies (peak kilovoltage (kVp) and/or filtration). Volumetric 3D image reconstruction and dual or triple energy 3D image decomposition can be executed using data from the CBCT scan. The invention allows for a variety of selections in energy and filtration associated with each source and the order of pulsing for each source ("firing pattern"). The (Continued)

motivation for distributing the sources along the z direction in CBCT includes extension of the longitudinal field of view and reduction of cone-beam artifacts.

20 Claims, 8 Drawing Sheets

(52) U.S. Cl.
CPC ............ *A61B 6/4085* (2013.01); *A61B 6/482* (2013.01); *A61B 6/5205* (2013.01); *A61B 6/5235* (2013.01); *A61B 6/505* (2013.01)

(56) References Cited

U.S. PATENT DOCUMENTS

| | | |
|---|---|---|
| 8,509,380 B2 | 8/2013 | Pelc et al. |
| 2005/0100126 A1 | 5/2005 | Mistretta et al. |
| 2006/0045234 A1* | 3/2006 | Pelc ........................ A61B 6/032 378/9 |
| 2007/0133744 A1 | 6/2007 | Bijjani |
| 2009/0252285 A1 | 10/2009 | Shapiro et al. |
| 2010/0002830 A1 | 1/2010 | Proksa et al. |
| 2011/0002439 A1 | 1/2011 | Zhang |
| 2011/0176659 A1 | 7/2011 | Rogers et al. |
| 2012/0099709 A1 | 4/2012 | Thesen et al. |
| 2015/0150524 A1* | 6/2015 | Yorkston .............. A61B 6/4007 378/9 |
| 2016/0193366 A1* | 7/2016 | Yeh .................... A61K 49/0409 424/9.4 |

FOREIGN PATENT DOCUMENTS

| | | |
|---|---|---|
| KR | 10-0064442 A | 7/2008 |
| WO | WO-2010/070554 A1 | 6/2010 |

\* cited by examiner

DUAL-ENERGY CONE-BEAM COMPUTED TOMOGRAPHY WITH A MULTIPLE SOURCE, SINGLE-DETECTOR CONFIGURATION

CROSS REFERENCE TO RELATED APPLICATION

This is a national stage application under 35 U.S.C. § 371 of PCT/US2014/067208 filed Nov. 25, 2014, the entire contents of which are incorporated herein by reference and this application claims the benefit of U.S. Provisional Patent Application No. 61/909,115 filed on Nov. 26, 2013, which is incorporated by reference, herein, in its entirety

GOVERNMENT SUPPORT

This invention was made with Government support under Grant No. AR062293 awarded by the National Institutes of Health (NIH). The Government has certain rights in this invention.

FIELD OF THE INVENTION

The present invention relates generally to medical imaging. More particularly, the present invention relates to imaging using computed tomography.

BACKGROUND OF THE INVENTION

Existing methods for dual-energy or spectral tomography include, for example, fast kVp switching of a single source during rotation, multiple rotations of a single source (varying the kVp in each rotation); detector configurations providing energy discrimination in the detected signal (e.g., energy-discriminating photon counters or sandwich detectors); two (or more) x-ray sources each used in combination with a detector (e.g. a dual-source CT scanner involving two x-ray sources and two detectors); and most recently in development, a configuration of x-ray sources distributed in the axial plane (i.e. in the x direction orthogonal to the axis of rotation) and a single detector. However, none of the existing methods for dual-energy (or spectral) imaging configure x-ray sources along the z-direction, and therefore result in images with a shortened longitudinal field of view and higher incidence of cone-beam artifacts.

Accordingly, there is a need in the art for a method of dual-energy imaging with x-ray sources configured along the z-direction, in order to extend longitudinal field of view and reduction of cone-beam artifacts.

SUMMARY OF THE INVENTION

The foregoing needs are met by the present invention which provides a system for cone-beam computed tomography of a subject including three sources of x-ray energy. The system includes an x-ray detector configured and positioned to detect x-ray energy from the sources of x-ray energy. Additionally, the three sources of x-ray energy are distributed along an axis parallel to an axis of rotation of a gantry about an axis of the subject, and the three sources of x-ray energy are configured to have a firing pattern for delivering the x-ray energy.

In accordance with another aspect of the present invention, a first and a second of the three sources of x-ray energy operate at a same level of energy. A third of the three sources of x-ray energy operates at a distinct level of energy from the first and second of the three sources of x-ray energy. Each of the three energy sources is coupled with a source of filtration. Alternately first and second sources of filtration are nominally the same level of filtration, and a third source of filtration is a distinct level of filtration from the first and second sources of filtration. The three sources of x-ray energy can also be operated at distinct levels of energy, and the three sources of x-ray energy are operated at distinct levels of filtration. The firing pattern includes a single-detector readout between each energy pulse and each of the three sources of x-ray energy are configured to be fired in succession.

In accordance with another aspect of the present invention, a system for cone-beam computed tomography of a subject includes two or more sources of x-ray energy. The system also includes an x-ray detector configured and positioned to detect the x-ray energy from the two or more sources. The two or more sources of x-ray energy are distributed along a z-direction parallel to an axis of rotation of a gantry about a z-axis of the subject.

In accordance with still another aspect of the present invention, the system includes first and second sources of x-ray energy, and the first and second sources of x-ray energy are operated at distinct beam energies. The system also includes providing distinct filtration for the first and second sources of x-ray energy. The system can includes first, second, and third sources of x-ray energies. The first and third sources of x-ray energy are operated at the same energy and the second source of x-ray energy is operated at a distinct energy, and the first and third sources of x-ray energy are operated with the same filtration and the second source is operated with a distinct filtration. Alternately, the first second and third sources of x-ray energy are all operated at distinct energies, and a distinct filtration is applied to each of the first, second, and third sources of energy. The system includes a non-transitory computer readable medium programmed to reconstruct a volumetric three-dimensional image of the subject from data related to a region of support determined by an overlap of a volumetric beam of energy from each of the two or more sources of x-ray. The non-transitory computer readable medium is programmed to reconstruct a composite three-dimensional image of the subject. Additionally, the system is configured to apply a distinct firing pattern for each of the two or more sources.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 4A and 4B illustrate an image of an imaging system according to an embodiment of the present invention.

FIG. 4C illustrates a resultant image taken with the imaging system of FIGS. 4A and 4B, according to an embodiment of the present invention.

FIG. 4D illustrates an image of a patient with BME in extremities with CBCT and MRI.

FIG. 7B illustrates an image of a DE estimate of the soft tissue fraction superimposed on the composite image for two levels of dose and various settings of reconstruction filter.

DETAILED DESCRIPTION

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains, having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention is directed to a system and method for dual-energy (DE) or multiple-energy (spectral) cone-beam computed tomography (CBCT) using a configuration of multiple x-ray sources and a single detector. The x-ray sources are operated to produce x-ray spectra of different energies (peak kilovoltage (kVp) and/or filtration). Volumetric 3D image reconstruction and dual or triple energy 3D image decomposition or classification can be executed using data from the CBCT scan. The invention allows for a variety of selections in energy and filtration associated with each source and the order of pulsing for each source ("firing pattern"). The motivation for distributing the sources along the z-direction in CBCT includes extension of the longitudinal field of view and reduction of cone-beam artifacts. It should however, be noted that this configuration for dual-energy imaging is particularly compatible with an extremity CT scanner, but is of course not limited to this type of scanning device.

More particularly, an embodiment of the invention includes a scanner having an x-ray source configuration comprising 2 or 3 x-ray sources distributed along the z direction (parallel to the axis of rotation) and a single flat-panel detector. While the present embodiment includes a flat-panel detector other digital x-ray detectors such as CMOS, CCD, or any other suitable detector know to one of skill in the art can also be used. The source-detector combination rotates about the subject as is typical in computed tomography (or, alternatively, for a benchtop scanner configuration, the subject is rotated). A volumetric 3D image reconstruction is formed in a manner similar to that in conventional CBCT—for example, using filtered backprojection (FBP), other analytical reconstruction methods, and/or various model-based reconstruction (MBR) methods. Within a volumetric region of support determined by the overlap of volumetric beams, a dual-energy 3D image decomposition or classification (for a 2-source configuration) or a dual-energy or triple-energy 3D image decomposition or classification (for a 3-source configuration) can be formed. The volumetric regions outside the overlapping region of support (e.g., above or below in the z direction), allow conventional single-energy 3D image reconstruction. The invention allows for a variety of selections in energy and filtration associated with each source and the order of pulsing for each source ("firing pattern").

Figure 1A:
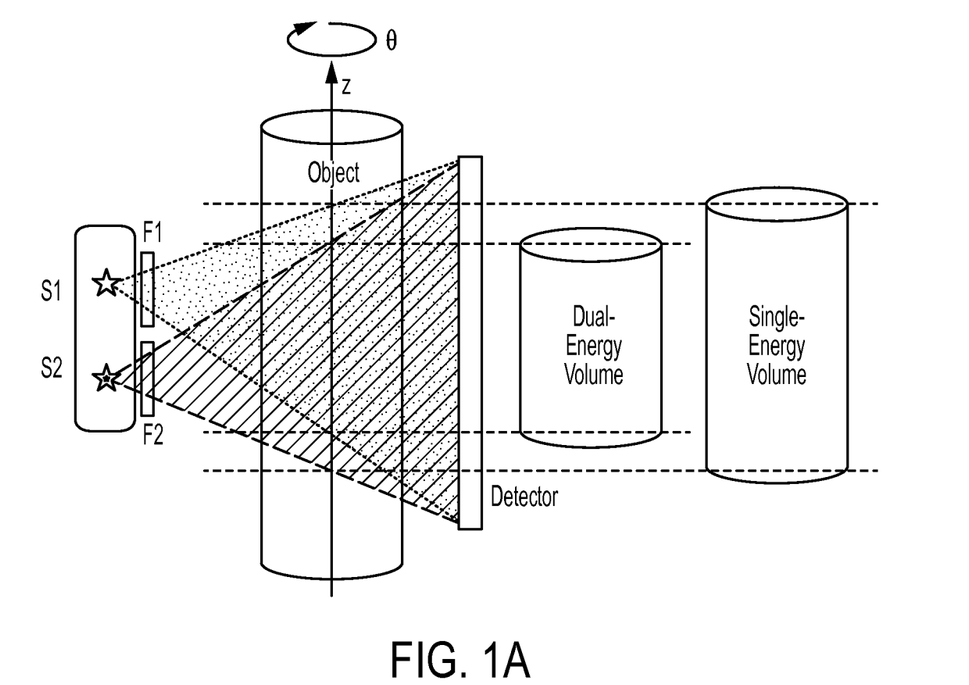
FIG. 1A illustrates a schematic diagram of a two-source configuration, according to an embodiment of the present invention.

FIG. 1A illustrates a schematic diagram of a two-source configuration, according to an embodiment of the present invention. The sources are denoted S1 and S2, operated at distinct beam energies (E1 and E2) and with the option for distinct filtration (F1 and F2). The single-energy image volume is the large region of support (illustrated in light gray) bounded by the union of volumetric beams. It should be noted that the Single-Energy Volume is a region corresponding to the composite image. The region outside of the composite region could be fused or stitched to the composite region if desired. The dual-energy image volume is the smaller region of support (illustrated in medium gray) bounded by the intersection of volumetric beams. Note that the "volumes" and "regions of support" mentioned throughout this document refer to the "fully sampled" region of the volume; a larger region of partially sampled volume (a "chamfer" above and below the regions denoted here) exists and would provide a degree of volumetric coverage beyond that demarked in these figures.

Figure 1B:
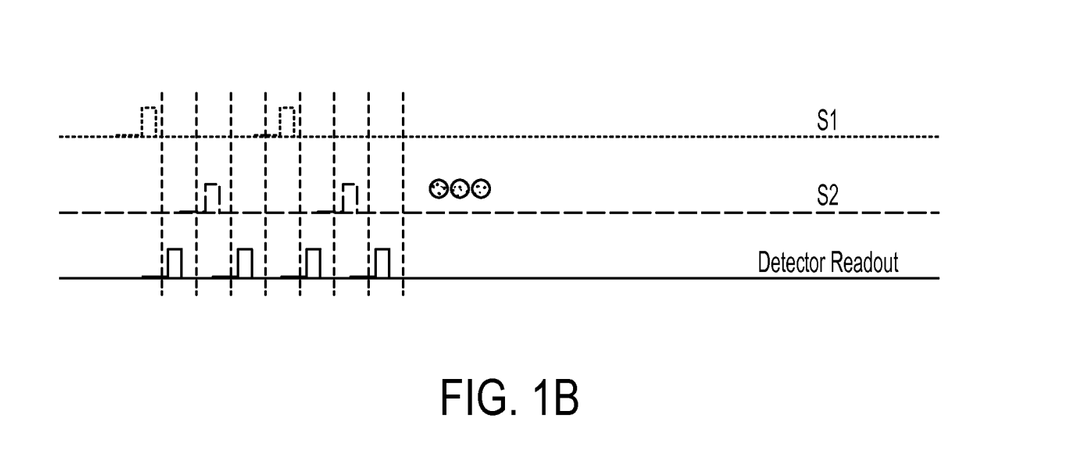
FIG. 1B illustrates a graphical view of an exemplary timing diagram, according to an embodiment of the present invention.

FIG. 1B illustrates a graphical view of an exemplary timing diagram, according to an embodiment of the present invention. FIG. 1B illustrates the sequence of x-ray pulses and detector readout in the 2-source configuration illustrated in FIG. 1A. A simple sequence or "firing pattern" is shown, involving a single detector readout in between each x-ray pulse, denoted S1-Read, S2-Read, S1-Read, . . . . Alternate firing patterns can also be used.

Figure 2A:
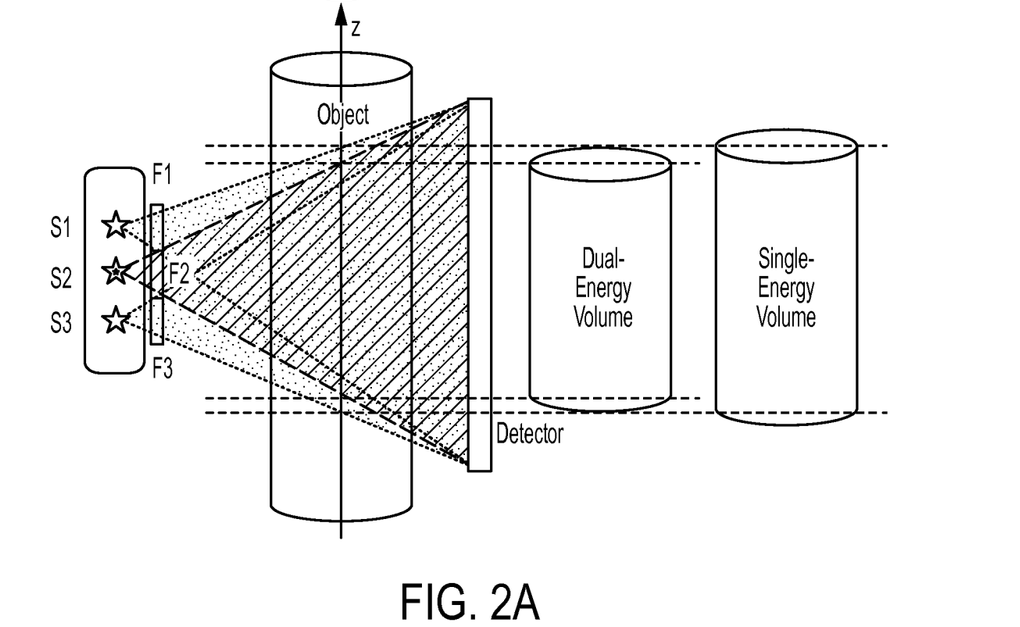
FIG. 2A illustrates a schematic diagram of a three-source configuration, according to an embodiment of the present invention.
Figure 2B:
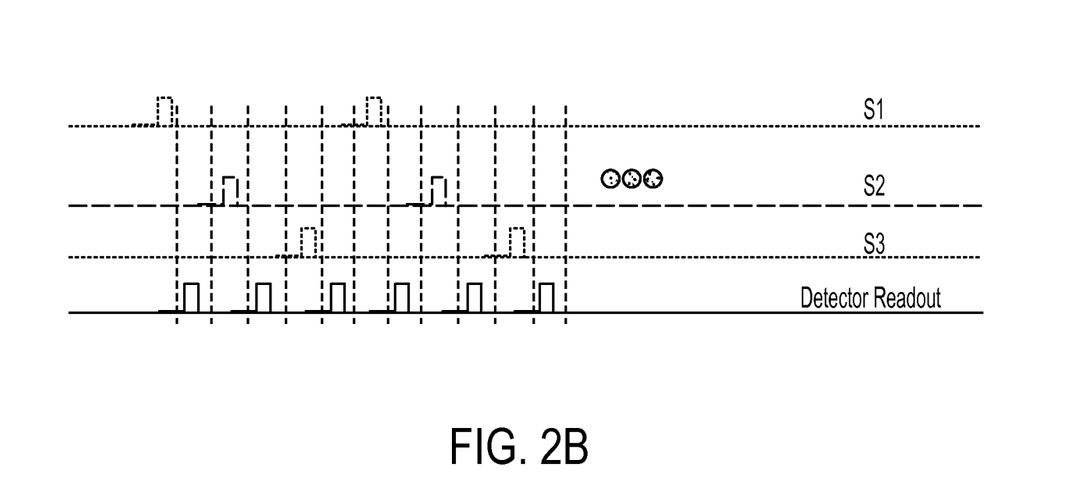
FIG. 2B illustrates a graphical view of an exemplary timing diagram for the three-source configuration, according to an embodiment of the present invention.

FIG. 2A illustrates a schematic diagram of a three-source configuration, according to an embodiment of the present invention. The energy sources are denoted S1, S2, and S3. S1 and S3 are operated at the same energy (E1=E3, and nominally the same filtration F1=F3), and S2 is operated at a distinct energy (E2) and filtration (F2). The invention allows for the "dual-energy" pair to be involve either S1 and S3 operating at high energy (and S2 at low energy)—or vice versa. Note that this 3-source configuration provides a larger dual-energy volume than the 2-source configuration illustrated in FIG. 1A. The note with respect to FIG. 1A regarding the "fully sampled" and partially sampled regions of support in each volume, also applies here with respect to FIG. 2A FIG. 2B illustrates a graphical view of an exemplary timing diagram for the three-source configuration illustrated in FIG. 2A, according to an embodiment of the present invention. FIG. 2B illustrates the sequence of x-ray pulses and detector readout in the 3-source configuration. A simple sequence ("firing pattern") is shown, involving a single detector readout in between each x-ray pulse, and each source fired in succession, denoted: S1-Read/S2-Read/S3-Read/ . . . . Alternative firing patterns are within the scope of the invention.

Figure 3A:
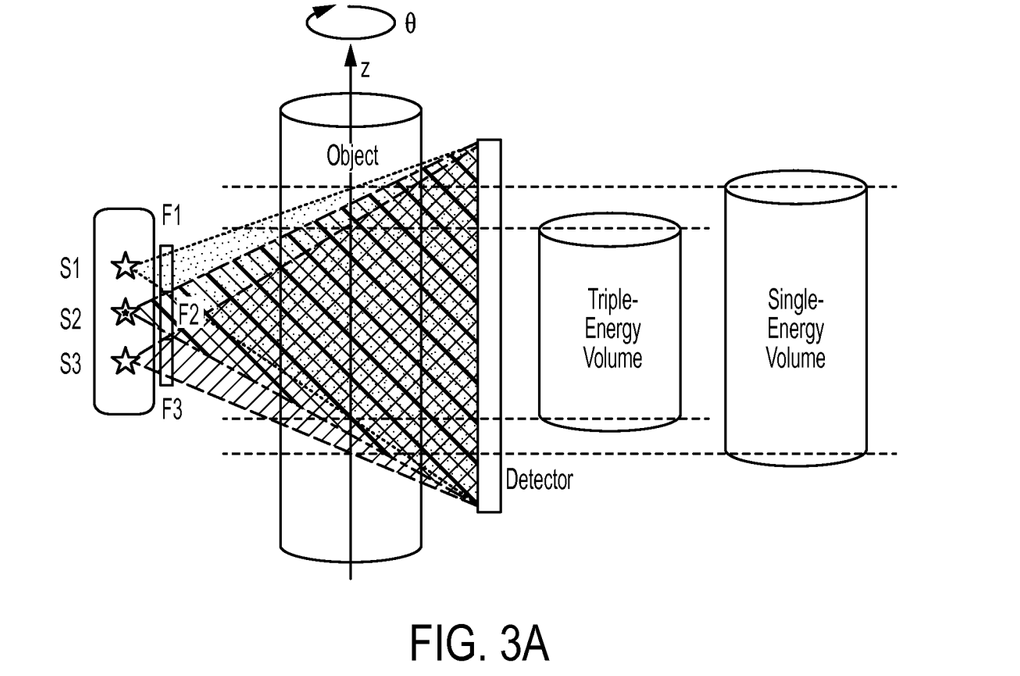
FIG. 3A illustrates a schematic diagram of another three-source configuration, according to an embodiment of the present invention.

FIG. 3A illustrates a schematic diagram of another three-source configuration, according to an embodiment of the present invention. S1, S2, and S3 are operated at different energies (E1, E2, and E3) and optionally different filtration (F1, F2, and F3). This configuration allows for "triple-energy" imaging within a volumetric region of support defined by the intersection of the three volumetric beams. The note with respect to FIG. 1A regarding "fully sampled" and partially sampled regions of support in each volume also applies here with respect to FIG. 3A.

Figure 3B:
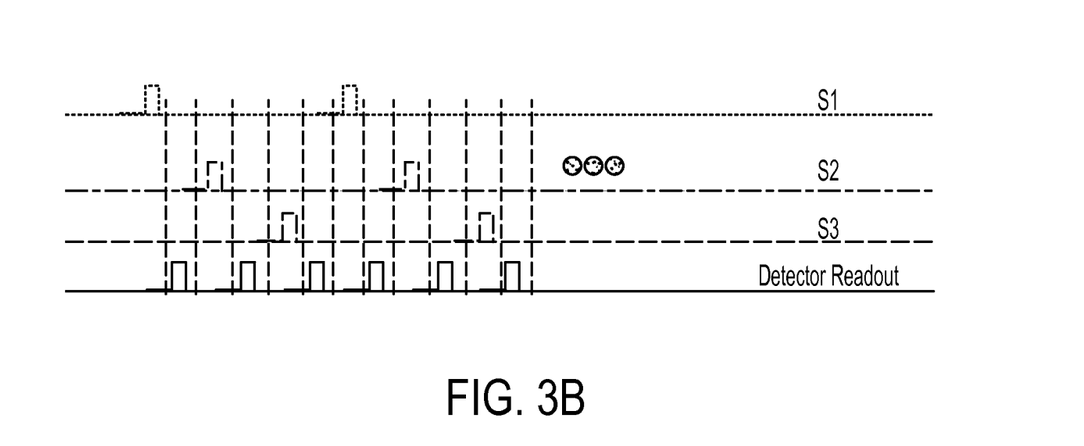
FIG. 3B illustrates a graphical view of an exemplary timing diagram for the three-source configuration, according to an embodiment of the present invention.

FIG. 3B illustrates a graphical view of an exemplary timing diagram for the three-source configuration illustrated in FIG. 3A, according to an embodiment of the present invention. FIG. 3B illustrates the sequence of x-ray pulses and detector readout in the 3-source configuration. A simple sequence ("firing pattern") is shown, involving a single detector readout in between each x-ray pulse, and each source fired in succession, denoted: S1-Read/S2-Read/S3-Read/ . . . . Alternative firing patterns are within the scope of the invention.

The methods for formation of the composite and dual- (or triple-) energy images involve (but are not limited to):

(a) Image-Based Material Classification. The image-based material classification approach described above should be considered known prior art in the general context of dual- (or triple-) energy imaging and is summarized here for purposes of completeness in how the novel source and detector configurations described above may be used for dual- (or triple-) energy imaging. Reconstruction of volumes V1 and V2 from the projections acquired with sources S1 and S2 using an analytical (FBP) or iterative model-based algorithm. Voxels in V1 and V2 representing the same location within the dual-energy support volume are identified through prior geometric calibration. For each of these voxels, the reconstructed values in V1 and V2 are denoted as $\mu_1$ and $\mu_2$, respectively. $(\mu_1, \mu_2)$ is considered as a point in a 2-dimensional space (feature space), where materials are represented by their x-ray attenuation measured by the S1 and S2 energy spectra (typically falling on straight lines as a function of concentration). The material of each of the $(\mu_1, \mu_2)$ voxels can be identified using clustering techniques in this feature space. The number of materials that can be identified is limited by how many distinct material "signatures" are present in the feature space; theoretically, one can expect two broad classes of biological tissue (for example, calcified and non-calcified) and additional classes corresponding to contrast agents (for example, iodine) if the S1 and S2 spectra are appropriately chosen with respect to their K-edges. The same methodology can be used with three sources S1, S2, S3, and three volumes V1, V2, V3, now involving a 3-dimensional feature space. This approach is likely most beneficial when at least one K-edge contrast agent is present.

(b) Image-Based Material Decomposition.

As in (a) the approach is started with identifying voxels common to V1 and V2, whose reconstruction values are denoted as $\mu_1$, $\mu_2$. For each of the voxels:

$\mu_1 = c_a \mu_{a,S1} + c_b \mu_{b,S1}$ $\mu_2 = c_a \mu_{a,S2} + c_b \mu_{b,S2}$, [1]

where $c_a$, $c_b$ are concentrations of the two materials of interest in the voxel and $\mu_{a,S1}$ and $\mu_{a,S2}$ etc. are the attenuation values of the two materials in beams S1 and S2. This system of equations is now solved to find the unknown concentrations. A third material can be included when augmented with a "volume conservation" condition $c_a + c_b + c_c = 1$ (i.e. no other materials are present in the sample) or when the third volume V3 is present.

(c) Direct Model-Based Material Decomposition. Note that this method differs from (a) in that a concentration of each of the materials is found for each of the voxels in the union of V1 and V2, instead of assigning each one of them to a single material. The disadvantage of (b) may be noise increase due to the inversion necessary to solve the system of equations. Again, the image-based material decomposition approach should be considered known prior art and is summarized here for purposes of completeness in how the novel source and detector configurations described above may be used for dual- (or triple-) energy imaging. Direct decomposition as described in (c) is likely the only way to achieve "projection-based" decomposition in this setup (as opposed to e.g. two axial-plane sources, where simpler pre-processing methods can be used for that purpose) because of the lack of redundant rays between the sources operated at different energies. While the idea of direct decomposition is not novel, its application in this context is likely novel and potentially significant in enabling this invention given the anticipated advantages of projection-based decomposition (e.g. reduction of beam hardening artifacts) over image-based approach. A model-based approach solving simultaneously for concentrations $c_a$, $c_b$ given the projection data $y_1$ and $y_2$ (from sources S1 and S2) without the intermediate reconstruction step as in (a) and (b) can also be used. The following forward model for mean measurements can be employed:

$$\begin{bmatrix} \bar{y}_1 \\ \bar{y}_2 \end{bmatrix} = \begin{bmatrix} I_{01} \exp\left(-\int c_a(x_1) \mu_{a,S1} + c_b(x_1) \mu_{b,S1} dx_1 \right) \\ I_{02} \exp\left(-\int c_a(x_2) \mu_{a,S2} + c_b(x_2) \mu_{b,S2} dx_2 \right) \end{bmatrix}, \quad [2]$$

where $c_a(x)$, $c_b(x)$ are unknown concentrations of the two materials of interest inside the union of V1 and V2 and the line integrals are appropriately computed over rays originating at S1 (denoted as $x_1$) and S2 (denoted as $x_2$). After adopting a noise model (e.g. Gaussian or Poisson), one can find the reconstructions $c_a(x)$ and $c_b(x)$ by maximizing a log-likelihood objective function, e.g. for a Gaussian model, an objective of the form:

$$\text{argmax}\left(-\begin{bmatrix} y_1 - \bar{y}_1(c_a, c_b) \\ y_2 - \bar{y}_2(c_a, c_b) \end{bmatrix} W \begin{bmatrix} y_1 - \bar{y}_1(c_a, c_b) \\ y_2 - \bar{y}_2(c_a, c_b) \end{bmatrix}^T\right), \quad [3]$$

where W is a weighting matrix carrying inverse variances of the measurements. Such likelihood-based objectives can be further modified with a regularization term to encourage desirable image properties and to control noise.

The methods described above, as well as any other suitable methods for dual-energy or spectral tomography known to or conceivable by one of skill in the art can be executed by programming a non-transitory computer readable medium. The non-transitory computer readable medium can reside on a computing device, such as a server, tablet, smartphone, PC computer, imaging device computing terminal, terminal station or any other suitable computing device known to or conceivable by one of skill in the art. The non-transitory computer readable medium can either be loaded directly onto a hard drive of the computing device, can be on a separate hard disk or CD-ROM, can be on the server described above, another independent server, a network, or any other suitable configuration known to or conceivable by one of skill in the art.

The method can also include creating a network between the server and the computing device in communication with the non-transitory computer readable medium. A user interface can be configured for the user to input information into the system as well as configured for the user to interact with the system.

Exemplary Implementations

Exemplary implementations of the present invention are described herein, in order to further illustrate the present invention. The exemplary implementations are included merely as an example and are not meant to be considered limiting. Any implementation of the present invention on any suitable subject known to or conceivable by one of skill in the art could also be used, and is considered within the scope of this application.

Figures 4A, 4D:
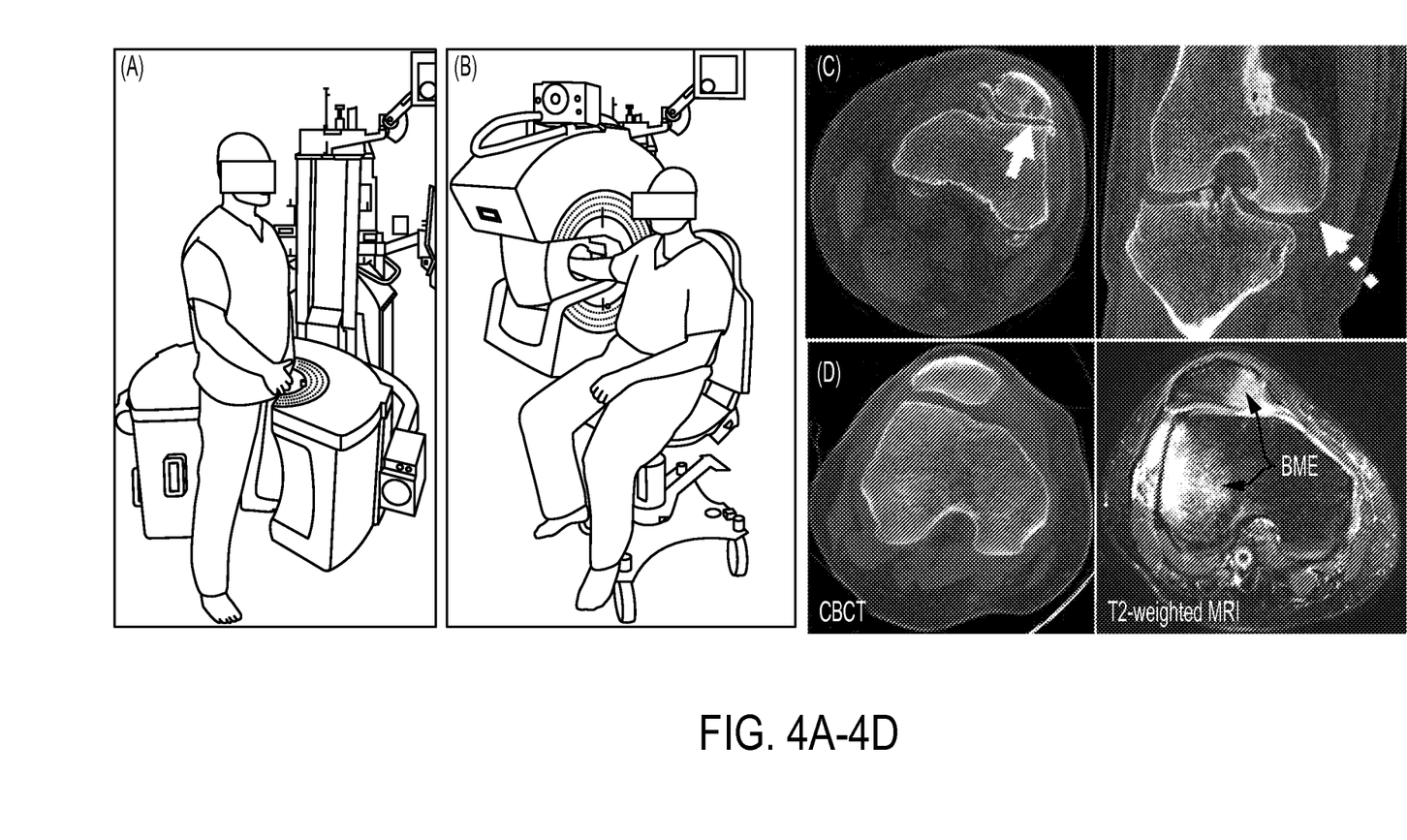

Bone marrow edema (BME) is a biomarker of arthritis (e.g. as a component in the Rheumatoid Arthritis MRI Score RAMRIS), occult fractures and other bone trauma, and bone infarcts and metastases. BME forms lesions of decreased fat (yellow marrow) content and increased fluid (soft-tissue-like) content in cancellous bone. The capability for evaluation of bone marrow lesions would be of particular value for recently introduced dedicated flat-panel detector (FPD) cone-beam CT (CBCT) systems for musculoskeletal imaging, such as the system described herein and shown in FIGS. 4A and 4B. FIGS. 4A and 4B illustrate an image of an imaging system according to an embodiment of the present invention. FIG. 4C illustrates a resultant image taken with the imaging system of FIGS. 4A and 4B, according to an embodiment of the present invention. The system provides high spatial resolution enabling e.g. detailed visualization of bone erosions (often associated with arthritis, solid arrow) and employs an innovative 3-source xray tube for reduction of cone-beam artifacts (see e.g. lack of artifacts at the tibial plateau, dashed arrow).

FIG. 4D illustrates an image of a patient with BME in extremities with CBCT and MRI.

Owing to the low radiation dose, simplified logistics, and high spatial resolution [e.g. excellent visualization of bone erosions in FIG. 4C], extremities CBCT provides an attractive platform for longitudinal imaging of arthritis and fracture healing, where monitoring of BME would be especially valuable.

Conventionally diagnosed in MRI, BME is challenging to detect in x-ray CT due to partial-volume effect from the surrounding trabecular matrix, as illustrated in FIG. 4D. Recently, Dual Energy (DE) CT was evaluated for BME with encouraging results using a Virtual Non-Calcium technique similar to the Virtual Non-Contrast imaging known from other DE CT applications. Compared to the previously investigated DE CBCT of iodine enhancement in the joints, DE evaluation of BME involves a more challenging task of discrimination of endogenous materials, i.e. fat, soft-tissue and bone (calcium). The performance for DE CBCT in this scenario was investigated in realistic simulation studies with anatomical phantoms and in test-bench experiments. The 2nd generation CBCT system of FIGS. 4A and 4B is equipped with an innovative x-ray tube with three sources arranged in a vertical (longitudinal) configuration for extended field-of-view and reduction in cone-beam artifacts, as illustrated in FIG. 4B. This novel source configuration is evaluated in single-rotation DE imaging without the need for a filter wheel by operating the three sources at different energy and filtration.

Figure 5:
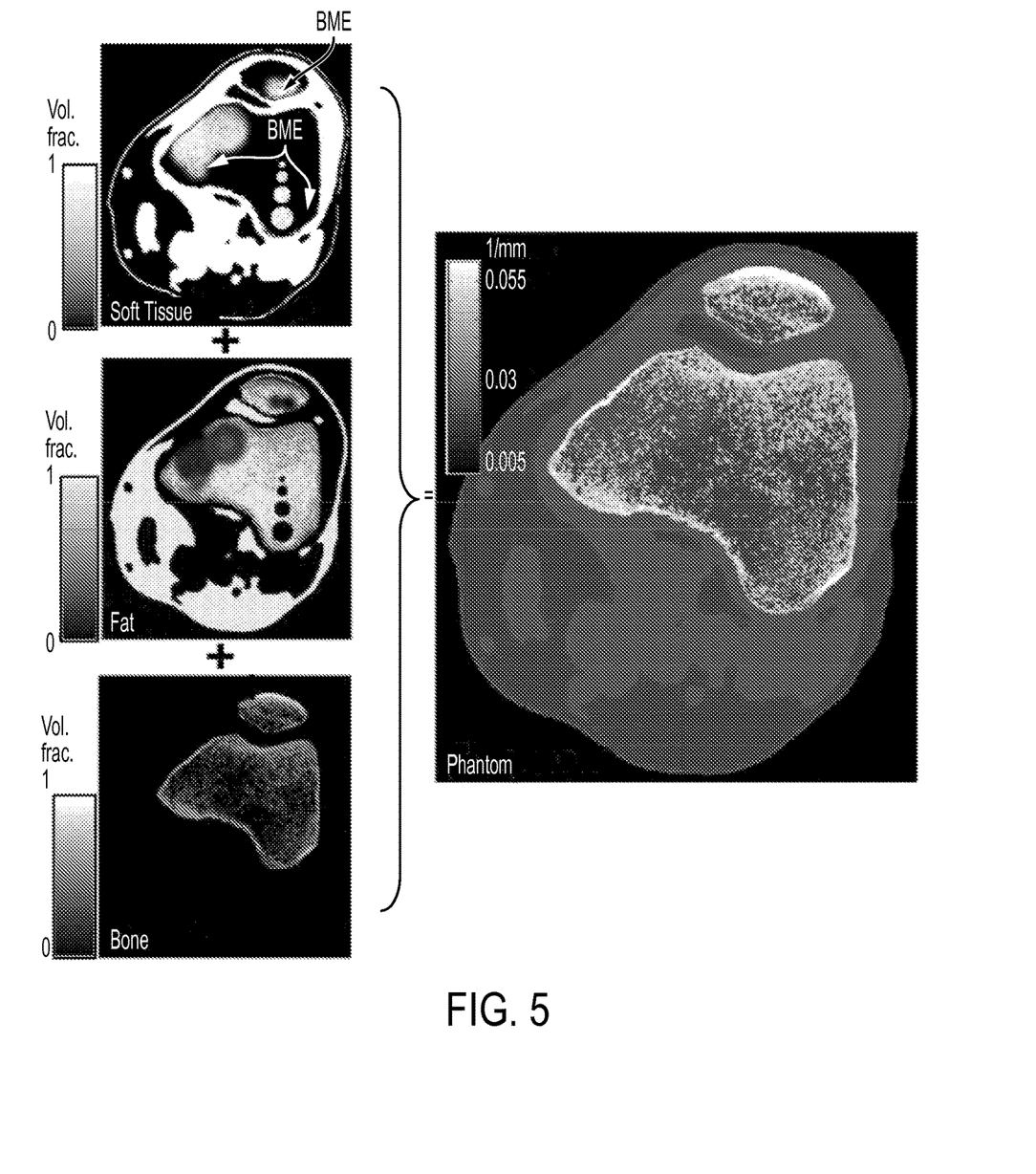
FIG. 5 illustrates images of a digital BME phantom, according to an embodiment of the present invention.

Initial investigation of BME detection involved a computer simulation study with a digital BME knee phantom to assess baseline DE CBCT performance in a realistic anatomical context. The phantom was developed from a high-resolution (voxel size: 0.125 mm) CBCT image of a knee. The reconstruction was segmented into soft tissue, fat, and bone (FIG. 5), and volume fraction of each material was assigned to the voxels. FIG. 5 illustrates images of a digital BME phantom, according to an embodiment of the present invention. Volume fractions of base materials (yellow: soft tissue, green: fat, white: cortical bone) were obtained from a CBCT volume. Trabecular bone was represented as a mixture of bone and fat. BME was simulated by replacing fat with soft-tissue. In particular, the voxels within the cortical boundaries of patella, tibia, and femur were represented as a mixture of fat and cortical bone (with no soft tissue allowed) emulating the composition of trabecular bone; the volume fractions of the base materials were determined from the attenuation values. Subsequently, regions of edema were added by replacing the fat in a region of trabecular bone with soft tissue, as indicated in the soft tissue image of FIG. 5.

In addition to the diffuse BME lesions in the femur and patella, a contrast-detail soft-tissue pattern consisting of 4 spheres of 2.5-10 mm diameter separated by 3.75 mm was also included in the femur. Polyenergetic projections with realistic FPD response (assuming ~0.5 mm CsI:Tl) were computed using x-ray spectra and material attenuation data provided in the Spektr package. The high-energy (HE) beam was 105 kVp (+0.2 mm Cu, +0.25 mm Ag), and the low energy beam was 60 kVp (+0.2 mm Cu), selected to fall within the voltage limits of the extremities CBCT x-ray source. The bare-beam photon fluence for the HE and LE beams was varied from 104-105 x-rays/pixel. Based on the estimates obtained from Spektr, a fluence of 104 x-rays/pixel corresponds to ~0.14 mAs exposure for the LE beam and ~0.08 mAs exposure for the HE beam. Voxel size was 0.125 mm, and detector pixel size was 0.388 mm. 360 projections were simulated at 1° increments. The geometry of the scanner in FIGS. 4A and 4B was used: Source-Axis Distance (SAD) of ~440 mm and Source-Detector-Distance of SDD ~560 mm. The focus of this study was baseline performance of DE CBCT in BME imaging, so only a double-scan, single-source acquisition was considered. Simulated projections were reconstructed with FBP with a Hann apodizer onto 0.25 mm voxels (providing a realistic approximation of partial volume averaging).

Figure 6A:
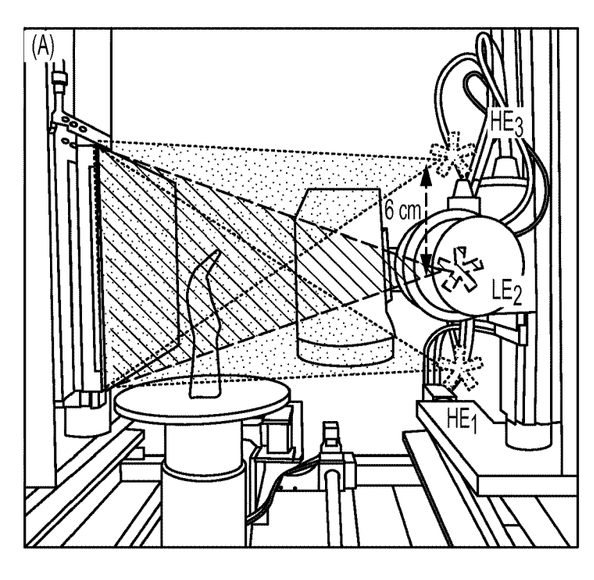
FIG. 6A illustrates an experimental CBCT bench emulating the three-source CBCT system, with the HE data acquired as a combination of exposures with the source in the inferior and superior positions ($HE_1$ and $HE_3$), and the LE data collected with the source in the central axial position ($LE_2$).
Figure 6B:
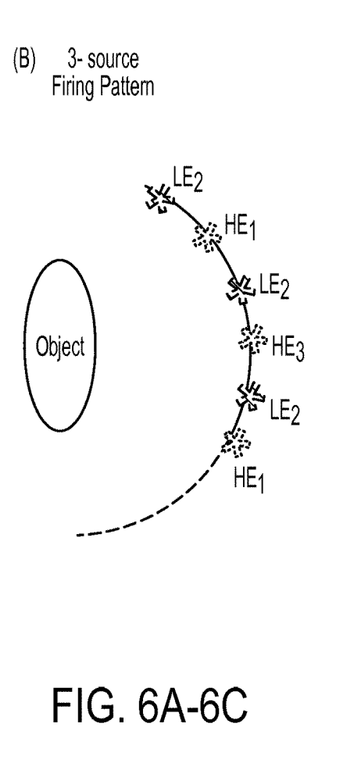
FIG. 6B illustrates a schematic diagram of a firing pattern of the three sources.
Figure 6C:
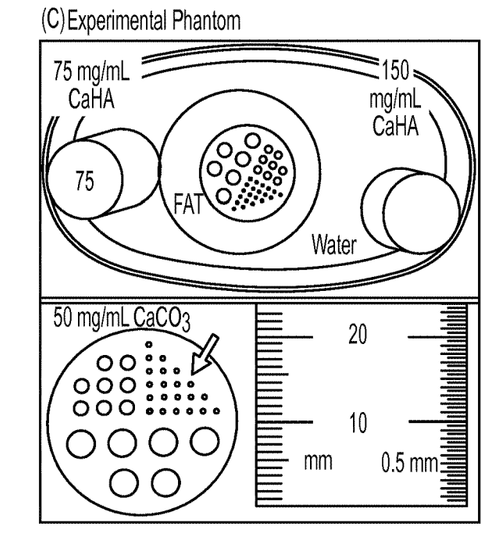
FIG. 6C illustrates an image of the three material phantom, with a bone cavity submerged in alcohol (simulating fat) to emulate trabecular bone.

FIG. 6A illustrates an experimental CBCT bench emulating the three-source CBCT system, with the HE data acquired as a combination of exposures with the source in the inferior and superior positions ($HE_1$ and $HE_3$), and the LE data collected with the source in the central axial position ($LE_2$). FIG. 6B illustrates a schematic diagram of a firing pattern of the three sources. FIG. 6C illustrates an image of the three material phantom, with a bone cavity submerged in alcohol (simulating fat) to emulate trabecular bone. Experimental studies involved a test-bench [FIG. 6A] configured to replicate the geometry of the extremities CBCT system, with the same SAD and SDD as in the simulation study and the same LE and HE x-ray spectra (60 kVp and 105 kVp+0.25 mm Ag). The HE was acquired at 0.2 mAs/frame, the LE at 0.5 mAs/frame. The FPD was a PaxScan 4030 (Varian Imaging Products, Palo Alto, Calif.) with a ~0.5 mm CsI:Tl operated with 2×2 pixel binning (0.388 mm pixel pitch). Projections were acquired at 1o increments with a 10:1 antiscatter grid (Jungwon Precision Industrial, South Korea) in place. In addition to a single source, doublescan trajectory (360 frames in the LE and HE data), a single-scan configuration with 3 longitudinally arranged sources was implemented [FIG. 6B]. The proposed scanning protocol involves LE data acquired with the source located in the central axial plane (source position "2" in FIG. 6A) and collecting full rotation at 1° steps. The inferior and superior sources (positions "1" and "3" in FIG. 6A) were offset by +/−6 cm from the axial plane and collected the HE data, firing alternately in between the LE exposures at 1° steps, as shown in FIG. 6B. During the complete scan, 180 HE frames were acquired with each of the peripheral sources. The total dose in the HE scan was the same as for the HE data in a single source, double-scan scenario. The 3-source system was emulated by an appropriate vertical translation of the x-ray tube for the acquisition of each of the LE and HE datasets. Reconstructions were performed with FBP with a Ramp filter on a 0.25 mm voxel grid. HE volume of the three-source data was obtained by averaging the HE1 and HE3 reconstructions. (Equal weighting of the two volumes is justified by the symmetric arrangement of the sources about the central plane). Experimental studies involved a "wrist" phantom (~9 cm×5 cm) with two bone densitometry inserts (75 mg/mL and 150 mg/mL CaHA) and ~3 cm diameter vial of alcohol (simulating fat) with a submerged bone mimicking insert (50 mg/mL CaCO3) containing a pattern of 1-4 mm cavities filled with the surrounding alcohol to emulate the mixture and bone and fat in the trabecular matrix [FIG. 6C].

Three-material DE decomposition was obtained from the pairs of HE and LE reconstructions by solving the well-known system of linear DE equations for volume fractions of soft tissue, fat, and bone in each voxel combined with equation requiring the fractions of the three base materials to add to unity. A linear least squares method with a positivity constraint was employed. The attenuation values of base materials in the simulation study were estimated from separate reconstructions of a cylindrical calibration phantom. In the experimental stud, the attenuation of fat (alcohol) and soft-tissue (water) were computed from regions-of-interest (ROIs) placed in the LE and HE reconstructions (similar to what can be done in patients using known regions of fat and soft-tissue). The LE and HE attenuation coefficients of (pure) Calcium were also computed from reconstruction ROIs by examining the slope of the line defined by measured attenuation of water and the 150 mg/mL bone densitometry insert. Future studies will investigate calibration integrated in the scanner gantry as shown earlier for CBCT bone densitometry.

The quality of DE decomposition in the simulation study was evaluated using metrics of binary decision theory. Elliptic ROIs were defined around each of the circular regions in the BME contrast-detail pattern. The ROIs contained equal number of voxels with a soft tissue fraction >50% (positive population) and voxels containing no soft-tissues. The true positive (TP) voxels where those that belonged to the positive population and were estimated by DE as having >30% fraction of soft-tissue (note that this fraction can potentially serve as a decision threshold in ROC-type studies). True negatives (TN) corresponded to voxels with <30% soft-tissue fractions that indeed belonged to the negative population. Overall performance of the decomposition is reported as accuracy [Acc=(Sensitivity+Specificity)/2] computed jointly over all ROIs in the contrast-detail BME pattern ($Acc_{comb}$).

Figures 7A, 7C:
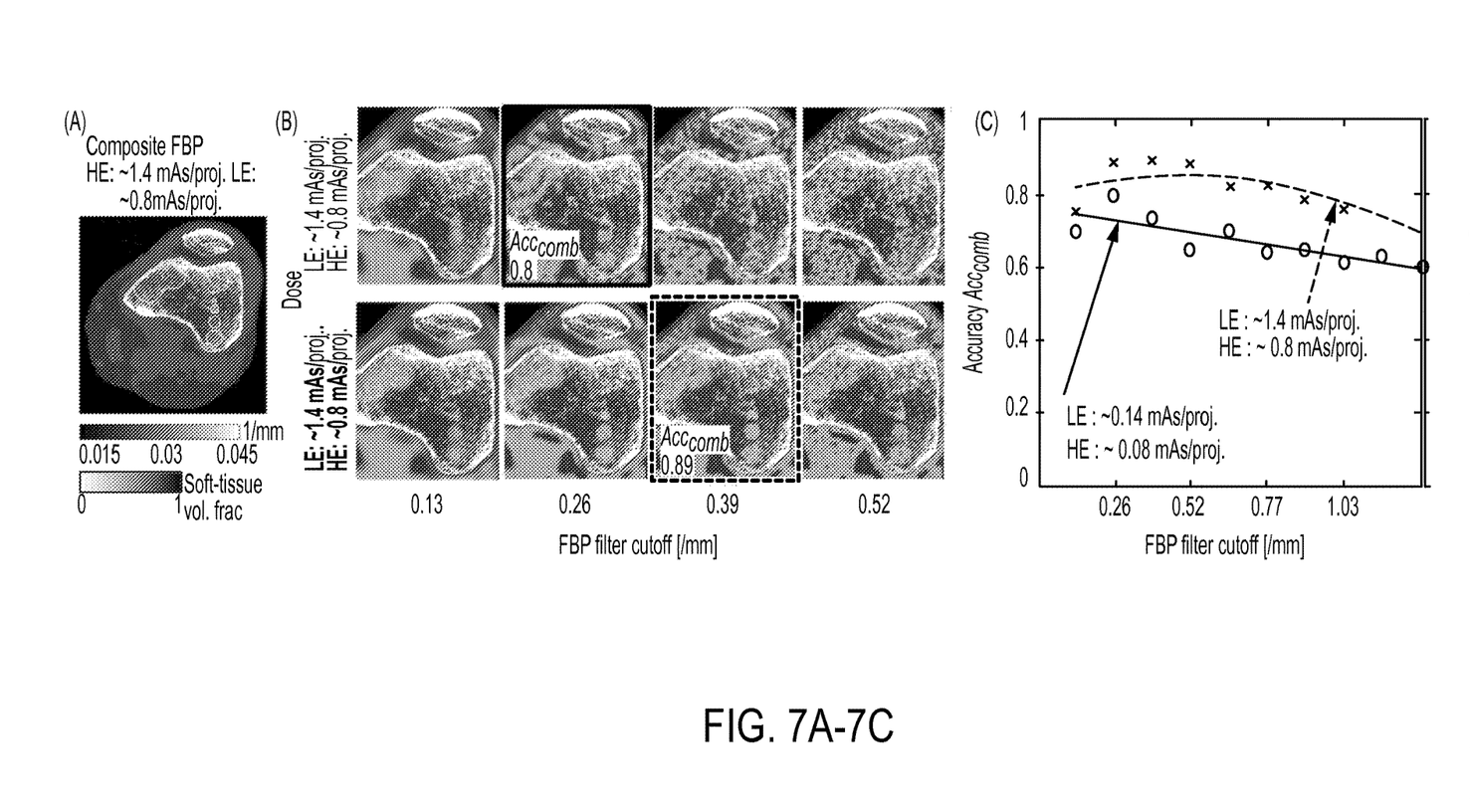
FIG. 7A illustrates a composite image of the BME phantom.
FIG. 7C illustrates an graphical view showing combined accuracy of the BME contrast-detail pattern (4 soft-tissue spheres in the right femoral condyle).

FIG. 7A illustrates a composite image of the BME phantom. Note the difficulty in identifying BME in single energy CBCT. FIG. 7B illustrates an image of a DE estimate of the soft tissue fraction superimposed on the composite image for two levels of dose and various settings of reconstruction filter. BME is readily identifiable in the DE decomposition as areas of soft tissue within trabecular bone. FIG. 7C illustrates an graphical view showing combined accuracy of the BME contrast-detail pattern (4 soft-tissue spheres in the right femoral condyle).

More particularly, FIG. 7A illustrates a composite FBP reconstruction (equally weighted sum of the LE and HE volumes) of the BME phantom, demonstrating the difficulty in detecting BME from the surrounding trabecular context. In FIG. 7B, soft-tissue volume fractions obtained with DE decomposition from pairs of LE and HE images computed with a variable FBP cutoff (equal for LE and HE) are overlaid on the composite image. The large, diffuse BME lesion on the left of the femur is readily identifiable in the DE decomposition for both dose levels (top and bottom rows), especially at lower cutoff values. The contrast-detail BME pattern visibility is hampered at very low cutoff frequencies by the reduction of the apparent soft-tissue fraction due to blur (reduced TP fraction) and for high cutoff frequencies due to noise (reduced TP fraction and increasing the fraction of false positives). As shown in FIG. 7C, optimal accuracy of ~80% is achieved at the lower imaging dose (~36 mAs for both beams, solid black line) at the FBP kernel cutoff of 0.26 mm-1, where the two largest contrast-detail inserts are distinguishable [FIG. 7B, top row]. At the ~10× increased dose (magenta dashed line), the optimal FBP cutoff increases to 0.89 mm-1 yielding Acccomb=0.89. The corresponding decomposition [bottom row in FIG. 7B] clearly identifies the inserts down to the smallest diameter of 2.5 mm.

Figure 8:
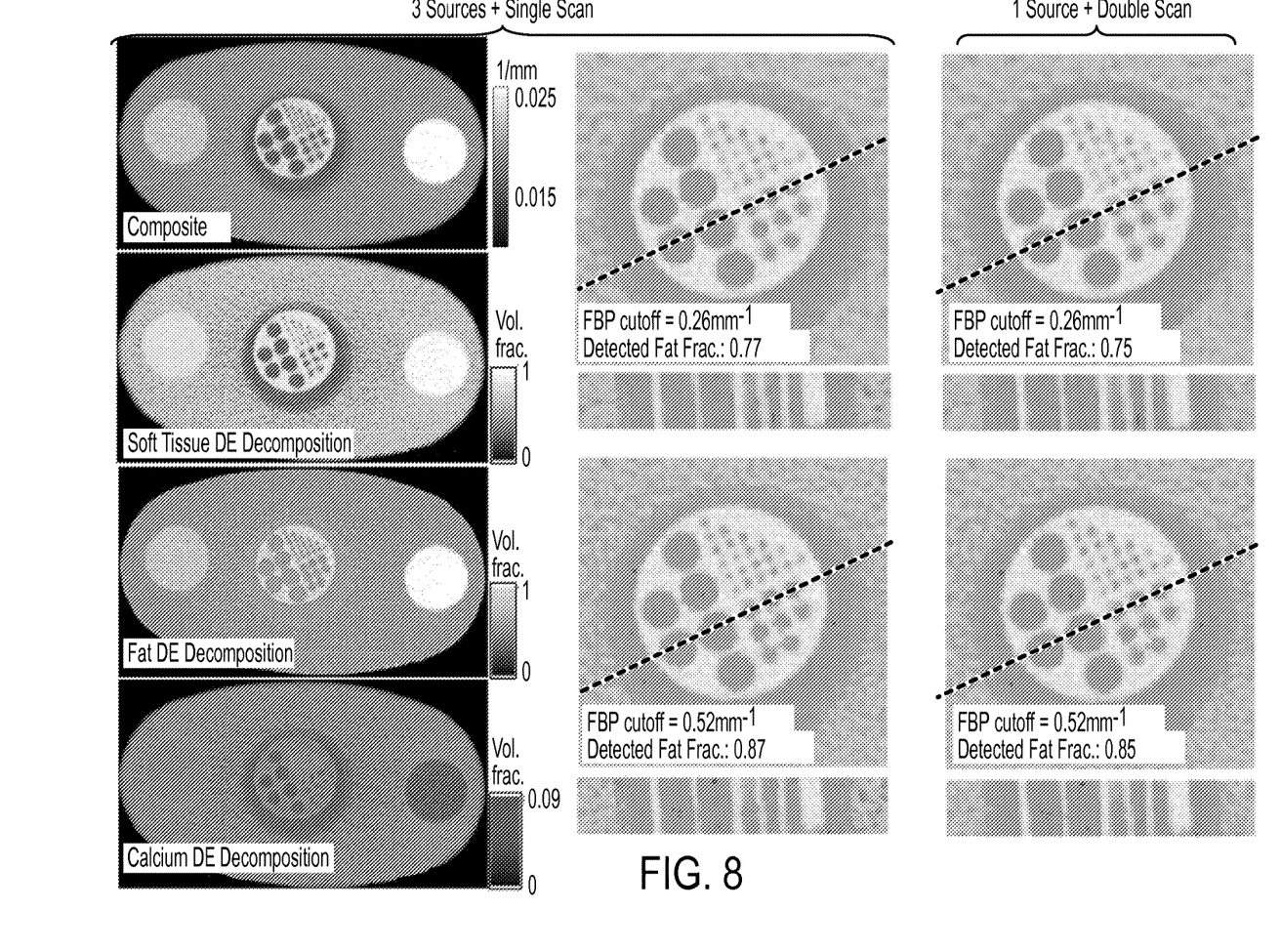
FIG. 8 illustrates images of experimental results according to an embodiment of the present invention.

FIG. 8 illustrates images of experimental results according to an embodiment of the present invention. Left: composite image and DE material maps acquired using the 3-source configuration. Excellent discrimination of calcium, water (soft-tissue) and alcohol (fat) is achieved. Magnified view of the bone cavity insert submerged in alcohol is shown with overlays of fat (green) and soft-tissue (yellow) DE maps. The insert is compared for the 3-source and single source acquisitions (center and right) and for two values of the FBP cutoff. 6 mm thick oblique trans-axial cut is shown underneath each axial image. On the left, a composite volume obtained from the LE and HE reconstructions acquired with the three axial source configuration in the alternating firing pattern of FIG. 6B is compared to the results of DE decomposition of the same projection data. The soft tissue (water) image does not show significant enhancement in the regions filled with alcohol (fat), but correctly indicates the presence of water in the bone densitometry inserts, where soft-tissue-like materials indeed form the bulk of the volume. Conversely, no fat is found in the densitometry rods, in agreement with their chemical composition. The alcohol-filled vial is correctly identified. The Ca image shows enhancement mainly in the densitometry inserts and reflects the difference in CaHA concentration in the two densitometry standards.

Magnified view of the alcohol-filled vial (an axial slice and an oblique ~6 mm.-thick trans-axial cut) is shown for two values of the reconstruction filter and both for the 3-source DE acquisition and for the more conventional single-source, double scan DE acquisition. Quality of the decomposition is assessed as the ratio of the total volume of voxels identified as fat inside the bone cavity insert to the volume expected for the design of the insert. There is almost no perceivable difference between the 3-source and single-source DE decompositions, with both acquisition patterns yielding a ~75% detected fat fraction at the cutoff of 0.26 mm-1 (where blur reduces decomposition performance for the 1 mm inserts) and ~85% detected fat fraction at the cutoff of 0.52 mm-1.

DE CBCT imaging allows for detection of BME patterns in trabecular bone that are not identifiable in single-energy scans. The novel three-source design of the x-ray tube allows single scan acquisition of the DE data and shows no loss in decomposition quality compared to a dual-scan, single-source acquisition, indicating that the longitudinal 3-source configuration does not suffer from cone-beam artifacts that may affect reconstruction-based DE decomposition. The proposed DE methodology suggests other applications involving assessment of bone composition and will support establishing extremities CBCT as a powerful tool for quantitative evaluation of bone and joint health.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A system for cone-beam computed tomography of a subject comprising:
   a first source, a second source and a third source of x-ray energy;
   an x-ray detector configured and positioned to detect x-ray energy from the first, second and third sources of x-ray energy;
   wherein the first, second and third sources of x-ray energy are distributed along an axis parallel to an axis of rotation of a gantry about an axis of the subject; and
   wherein the first, second and third sources of x-ray energy are configured to have a repeated firing sequence pattern for delivering the x-ray energy to the subject, and the first source of x-ray energy is configured to fire at a first time, the second source of x-ray energy is configured to fire at a second time and the third source of x-ray energy is configured to fire at a third time, the first time, the second time and the third time being different from each other, and
   wherein the first source of x-ray energy operates at a first energy, the second source of x-ray energy operates at a second energy, and the third source of x-ray energy operates at a third energy, and the first energy is different from at least one of the second energy and the third energy.

2. The system of claim 1, wherein the first energy and the second energy are a same level of energy.

3. The system of claim 2, wherein the third energy is different from the first energy and the second energy.

4. The system of claim 1, wherein each of the first, second and third sources of x-ray energy is coupled with a source of filtration.

5. The system of claim 4, further comprising a first source of filtration and a second source of filtration associated with the first and second sources of x-ray energy, respectively, the first and second sources of filtration being nominally at the same level of filtration.

6. The system of claim 5, further comprising a third source of filtration associated with the third source of x-ray energy, the third source of filtration being at a distinct level of filtration from the first and second sources of filtration.

7. The system of claim 1, wherein the first energy, second energy and third energy are different from each other.

8. The system of claim 7, wherein the first, second and third sources of x-ray energy are operated at distinct levels of filtration.

9. The system of claim 1, wherein the firing pattern includes a single-detector readout between each energy pulse and each of the first, second and third sources of x-ray energy are configured to be fired in succession.

10. A system for cone-beam computed tomography of a subject comprising:
    two or more sources of x-ray energy;
    an x-ray detector configured and positioned to detect the x-ray energy from the two or more sources; and
    wherein the two or more sources of x-ray energy are distributed along a direction parallel to an axis of rotation of a gantry about a z-axis of the subject,
    wherein a first source of x-ray energy and a second source of x-ray energy in the two or more sources of x-ray energy are configured to operate at distinct x-ray energies, or to operate with a distinct filtration, or both,
    wherein the first source of x-ray energy is configured to fire in a repeated sequence at a first time and the second source of x-ray energy is configured to fire at a second time, the first time and the second time being different from each other,
    wherein the first source of x-ray energy and the second source of x-ray energy together with the x-ray detector are configured to rotate about an object that is fixed or the object is configured to rotate while the first source of x-ray energy and the second source of x-ray energy together with the x-ray detector are fixed.

11. The system of claim 10, wherein the first and second sources of x-ray energy are operated at distinct x-ray energies.

12. The system of claim 11, further comprising a first filtration system and a second filtration system associated with the first and second sources of x-ray energy, respectively.

13. The system of claim 10, further comprising a third source of x-ray energy.

14. The system of claim 13, wherein the first and third sources of x-ray energy are operated at the same energy and the second source of x-ray energy is operated at a distinct energy.

15. The system of claim 13, wherein the first and third sources of x-ray energy are operated with a same filtration system and the second source is operated with a distinct filtration system.

16. The system of claim 13, wherein the first, second and third sources of x-ray energy are all operated at distinct energies.

17. The system of claim 13, wherein a distinct filtration system is applied to each of the first, second, and third sources of x-ray energy.

18. The system of claim 10, further comprising a non-transitory computer readable medium programmed to reconstruct a volumetric three-dimensional image of the subject from data related to a region of support determined by an overlap of a volumetric beam of energy from each of the two or more sources of x-ray.

19. The system of claim 10, further comprising a non-transitory computer readable medium programmed to reconstruct a composite three-dimensional image of the subject.

20. The system of claim 10, further comprising a firing controller configured to apply a distinct firing pattern for each of the two or more sources.

* * * * *